(12) United States Patent
Gibson

(10) Patent No.: US 6,869,468 B2
(45) Date of Patent: Mar. 22, 2005

(54) AIR TREATMENT APPARATUS

(75) Inventor: Phillip George Gibson, West Malling (GB)

(73) Assignee: Vent Master (Europe) Ltd., Rochester (GB)

( * ) Notice: Subject to any disclaimer, the term of this patent is extended or adjusted under 35 U.S.C. 154(b) by 7 days.

(21) Appl. No.: 10/182,915

(22) PCT Filed: Feb. 5, 2001

(86) PCT No.: PCT/GB01/00456

§ 371 (c)(1),
(2), (4) Date: Oct. 1, 2002

(87) PCT Pub. No.: WO01/56624

PCT Pub. Date: Aug. 9, 2001

(65) Prior Publication Data

US 2003/0121419 A1 Jul. 3, 2003

(30) Foreign Application Priority Data

Feb. 4, 2000 (GB) .............................................. 0002679

(51) Int. Cl.[7] ................................................ A61L 9/20
(52) U.S. Cl. ...................... 96/224; 55/DIG. 36; 95/19; 95/22; 96/400; 422/24; 422/121
(58) Field of Search ........................... 96/224, 400, 16, 96/18; 422/24, 121; 95/19, 22; 55/DIG. 36

(56) References Cited

U.S. PATENT DOCUMENTS 3,745,750 A * 7/1973 Arff ................................ 96/16
3,846,072 A 11/1974 Patterson
4,210,429 A * 7/1980 Golstein ....................... 96/142
5,042,457 A * 8/1991 Gallagher ............... 126/299 E
5,112,370 A * 5/1992 Gazzano ..................... 422/121
5,152,814 A * 10/1992 Nelson ......................... 96/224
5,523,057 A * 6/1996 Mazzilli ....................... 422/121
5,704,955 A * 1/1998 Giles ............................. 96/26
5,718,219 A * 2/1998 Boudreault ............. 126/299 E
5,891,399 A * 4/1999 Owesen ..................... 422/121
6,053,968 A * 4/2000 Miller .......................... 96/224
6,235,090 B1 * 5/2001 Bernstein et al. .............. 96/57
6,497,840 B1 * 12/2002 Palestro et al. ............... 422/24
2002/0144601 A1 * 10/2002 Palestro et al. ............... 95/273

FOREIGN PATENT DOCUMENTS

| DE | 19 08 450 | 9/1970 |
| DE | 27 32 859 | 2/1979 |
| DE | 28 17 772 | 10/1979 |
| EP | 0 461 310 | 12/1991 |
| WO | 94/08633 | 4/1994 |
| WO | 98/38462 | 9/1998 |

* cited by examiner

Primary Examiner—Richard L. Chiesa
(74) Attorney, Agent, or Firm—Ohlandt, Greeley, Ruggiero & Perle, L.L.P.

(57) ABSTRACT

An air extraction and treatment unit (2) is located above a source of contaminated air. The apparatus has a series of ultraviolet tubes (20) for treating the decontaminated air. The unit is arranged such that in use substantially no direct or reflected ultraviolet light is visible from outside the unit. Furthermore even when a removable filter (4) is removed, there is no direct line of sight to the ultra-violet sources.

8 Claims, 4 Drawing Sheets

AIR TREATMENT APPARATUS

This invention relates to apparatus for treating contaminated air such as is produced in commercial kitchens, e.g. to remove odours and the like therefrom.

The usual way to treat air laden with grease and odours which is produced by a cooking appliance is to extract air from above the appliance to the outside by means of an extraction unit mounted above the appliance. This extraction unit is generally in the form of a hood and includes a number of filters and/or particle traps to trap grease and other particles in the air. Some sort of deodorising means is also often included such as an activated carbon filter or a source of fragrant masking oil.

The problems with mechanical filters are that they tend to need regular replacement or cleaning and also that when laden with grease etc., they represent a significant fire hazard.

Proposals have been made to use ultra-violet light to decontaminate air in air extraction units of the type described above although it is understood that to date none has progressed beyond the prototype stage. In these arrangements ultra-violet tubes are provided above the air inlet behind the front wall of the unit. This front wall therefore hides the tubes from direct view. However since these units are fabricated from stainless steel, when the tubes are in operation light from them escapes through the air inlet and is reflected off the downwardly extending rear wall of the unit, thus making the light clearly visible.

The inventors have realised however that even reflected light from the UV tubes typically used in these applications is hazardous despite the previous tacit assumption to the contrary.

When viewed from a first aspect therefore the present invention provides an air extraction and treatment unit for mounting above a source of contaminated air, said unit comprising an air inlet through which said contaminated air is extracted in use, an air outlet through which decontaminated air is expelled in use, and an air treatment means disposed therebetween, said air treatment means having an ultra-violet light source, wherein the unit is arranged such that in use substantially no direct or reflected ultra-violet light is visible from outside the unit.

Thus it will be seen that in accordance with the invention, the hazards of exposure even to reflected ultra-violet (UV) light are substantially avoided. This means that such units can safely be employed at the source of contaminated air e.g. at a cooking appliance in a commercial or industrial kitchen even though someone may need to work very close to the unit whilst using the appliance. A person working in the vicinity of the unit will not necessarily even know that it contains a potentially hazardous UV radiation source. In accordance with the invention no particular special precautions need be taken.

Air is typically moved through units of the type to which the invention applies by a remote fan downstream of the unit, e.g. just before the decontaminated air is exhausted to the atmosphere. Commonly a single such fan will serve several air extraction and treatment units.

The unit may be arranged just with suitably positioned walls to avoid the escape of light from the unit. This is relatively easy to achieve for most of the walls of the unit. Of course however the air inlet must be in fluid communication with the exterior of the unit and therefore particular precaution is necessary to avoid the potential escape of UV light from any angle which might render it visible to a user. The region of the air inlet may be therefore be defined with suitably positioned walls.

In preferred embodiments however a filter disposed in the path of incoming air forms at least part of the barrier to light escaping. This filter is preferably arranged to remove relatively large particles, e.g. grease and/or fat, from the air passing through it. This is particularly beneficial since the inventors have realised that UV light is most efficient at removing odours as opposed to particles of fat and grease and furthermore that its efficiency at removing odours is enhanced if the grease and fat has already been removed from the air being treated.

In the most preferred embodiment the filter is of the type which forces air flowing therethrough to change direction abruptly. This arrangement has been found to be best for removing larger particles of fat and grease by means of a centrifuge effect without clogging the filter. Most preferably the filter is reusable and therefore requires at most periodic cleaning.

The filter may be permanently or semi-permanently fixed, i.e. with the intention that it is not removed by an ordinary user. Preferably though the filter is removable, e.g. for cleaning. As stated above, in preferred embodiments the filter provides at least part of the barrier against the escape of UV light. It follows therefore that if it is removed there will no longer be such a barrier. The inventors have realised that whilst direct UV light of the sort used to deodorise air can be hazardous with only brief exposures, light reflected from stainless steel parts is hazardous only with longer exposures.

Thus where the unit comprises a removable filter providing at least part of the light barrier, the rest of the unit is preferably arranged such that even with the filter removed no direct UV light from the unit is visible, i.e. only reflected light is visible.

Such a feature is considered to be inventive in its own right. Viewed from a second aspect therefore, the invention provides an air extraction and treatment unit for mounting above a source of contaminated air, said unit comprising an air inlet through which said contaminated air is extracted in use, an air outlet through which decontaminated air is expelled in use, a removable air filter disposed in the path of incoming air, and an air treatment means disposed downstream of the air filter and having an ultra-violet source, wherein when the air filter is removed there is no direct line of sight between the ultra-violet source and the outside.

Thus exposure to direct UV light can be avoided at the time of filter removal.

It will be appreciated that references herein to a removable filter cover at least both a filter which can be fully removed, e.g. for machine washing, and a filter which is removed from its normal operating position but is not fully detached from the rest of the unit, e.g. by hinging open for manual cleaning in situ.

It is further preferred that means are provided to reduce or interrupt the supply of power to the UV source in the event that such a filter is removed. Additionally or alternatively means are provided to interrupt or reduce the power in the event that any part of the unit is dismantled.

The means for interrupting or reducing the power may comprise a switch such as a microswitch or the like in the region of the removable filter or other removable part of the unit, but preferably comprises pressure sensing means which can sense the drop in pressure inside the unit if the filter or any other part is removed. This is beneficial since it means that the UV source can be switched off if any leak develops—even if not associated with an intentionally removable part.

In the preferred arrangement in which there is both a power supply reduction or interruption when the filter is removed, and no direct line of sight between the UV source and the outside, if there is a delay or malfunction in the operation of the former safety feature, the latter provides an additional safety feature.

It is also a preferred feature of the present invention that a baffle is provided which is arranged to direct incoming air across the whole area covered by the UV light source or sources. In one convenient embodiment it is this baffle which prevents direct light from the UV source escaping from the unit even when a removable filter is removed.

Downstream of the filter, there may be provided means to cause one or more further changes in the direction of air flow, to provide an additional fat and grease removal effect. Such means may comprise the baffle mentioned above.

Certain preferred embodiments of the present invention will now be described, by way of example only, with reference to the accompanying drawings in which.

Figure 1:
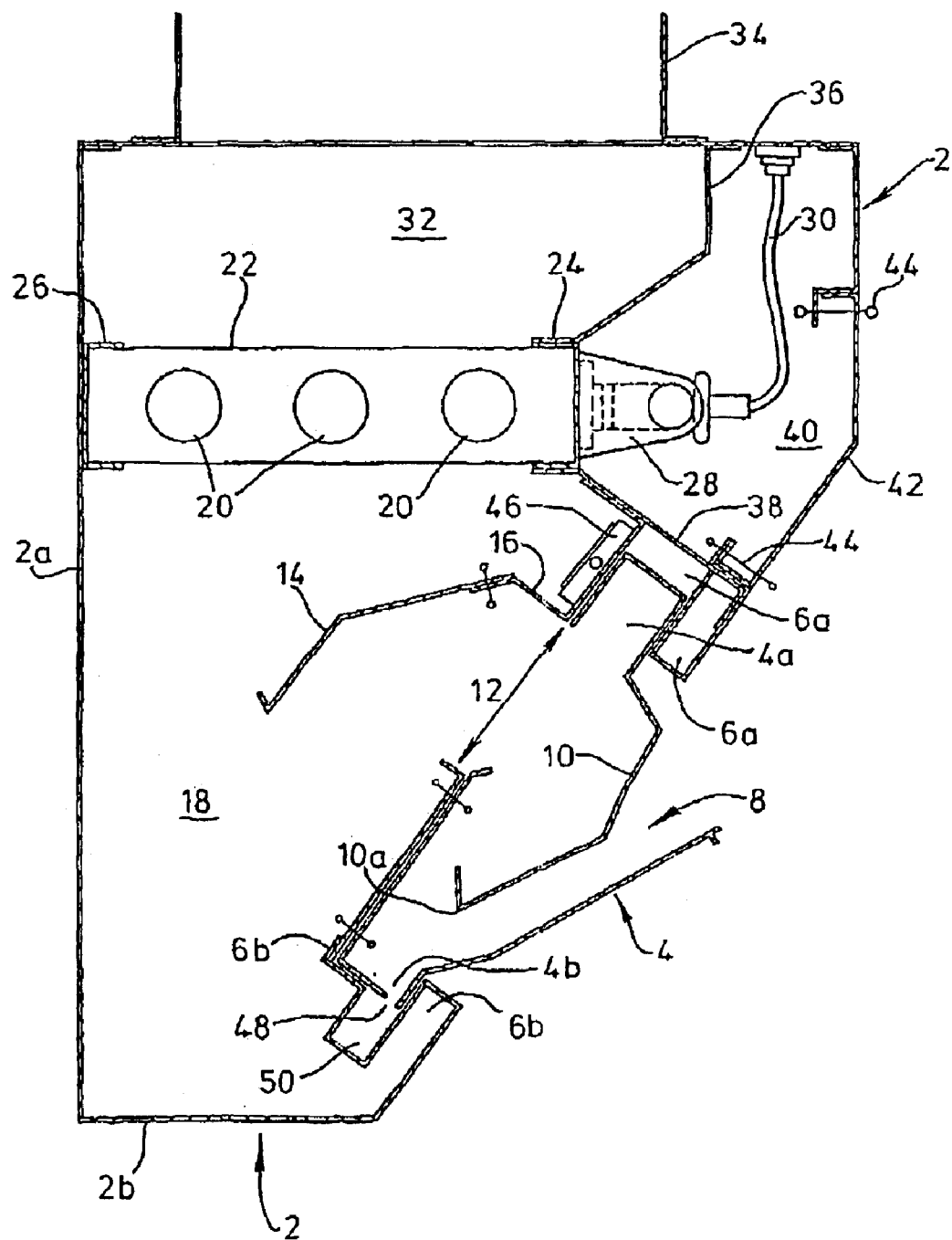
FIG. 1 is a cross-sectional view of an air extraction and treatment unit in accordance with the present invention.

Turning to FIG. 1, this shows a cross-section through an air extraction and treatment unit which is installed above a cooker in a commercial kitchen (not shown). The unit is generally encased in a stainless steel housing 2 which is attached to a wall along its rear wall 2a. A grease filter 4 is arranged towards the front of the unit. The filter has respective upper and lower extensions 4a, 4b which are received in corresponding slots 6a, 6b formed in the unit housing. The grease filter 4 has an air inlet opening 8 and an internal baffle 10 which depends from the rear edge of the opening 8. It will be seen from FIG. 1 that when the grease filter 4 is installed in the position shown, it covers the opening 12 in the lousing of the unit which would otherwise be present.

Between the opening 12 and the rear wall 2a of the housing there is defined a plenum 18. A baffle 14, which is fixed to a short extension 16 of the wall defining the opening 12, extends into the plenum 18. The baffle 14 is bent so as to direct air entering the plenum diagonally downwardly. At the top of the plenum 18 is an array of UV tubes 20 which are held in a cassette 22. The cassette 22 is slidably received in front and rear brackets 24, 26 respectively. A series of clips (not shown) is provided to hold the cassette 22 in place. Electrical connection to the tubes is made by means of a removable electrical connector 28 and electrical supply cable 30.

Above the UV cassette 22 is a further space 32 which communicates with an air outlet duct 34. The front of the space 32 is delimited by a wall 36 which, in conjunction with the forward UV cassette 24 and a similar wall 38 defining part of the lower plenum 18, defines a front access space 40 separated from the air flow in which the electrical connector 28 and cable 30 are housed. The front panel 42 which provides access to this space is secured to the main housing 2 of the unit by means of a series of special screws 44 (shown only schematically). These screws have specially shaped heads in order to ensure that only qualified service personnel possessing the right tool are able to remove the panel 42 and therefore gain access to the UV cassette 22.

Finally, a pressure sensor 46 is disposed in the plenum 18 adjacent the upper slot 6a for receiving the grease filter 4. This sensor is electrically connected to a control device (not shown) for switching off the electrical supply to the UV cassette 22 in the event that a drop in pressure in the plenum 18 is detected. This will arise for example if the grease filter 4 is removed or if the front panel 42 is removed since the enclosed space 40 is not pressure-sealed from the plenum 18 or space 32.

Operation of the unit will now be described. Reference is made to FIG. 1, but also to FIG. 2 which is the same as FIG. 1 but with the reference numerals omitted for clarity and the pattern of air flow marked on.

A fan (not shown) downstream of and in fluid is communication with the air outlet duct 34 creates a large negative pressure in the unit which sucks air through it. Air emanating from the cooker and laden with grease, fat and other organic substances is therefore drawn upwardly and through the air inlet opening 8 in the grease filter 4. The air is forced to flow around the internal baffle 10 in the grease filter and in particular around the sharp angled bend 10a at the lower end thereof. This sharp change of direction causes larger particles of grease as fat to be thrown out of the air stream and into the recess 4b in the grease filter.

The collected grease/fat will tend to remain molten due to the relatively high temperature of the walls of the grease filter and therefore drains through the discharge hole 48 into a recess 50 in the main housing.

Although not visible from the Figures, the recess 50 is inclined in a longitudinal direction so that the molten grease and fat collects in a designated sump and may be easily removed. Again, the relatively high temperature of the metal walls of the recess 50 keep the grease/fat molten.

Once the air has passed around the distal end 10a of the internal baffle 10, it passes back up the rear half of the grease filter 4 and exits through the opening 12 into the main plenum 18. The baffle 14 disposed in this plenum directs the air diagonally downwardly towards the bottom rear corner of the plenum 18. However, the negative pressure induced by the fan draws the air generally upwardly and therefore causes it to curl around the distal edge of the baffle 14 and towards the UV tubes 20. The air is drawn over the surfaces of the UV tubes 20.

The UV light causes ozone to be generated from oxygen present in the air and the ozone proceeds to oxidise the organic contaminants present in the air. The UV radiation also breaks down the larger organic substances through the process of photolysis. These processes are highly effective at removing odours from the air. Once odours and other organic substances have been removed, the air passes up into the space 32 and then through the outlet duct 34 from which it may be exhausted safely to the atmosphere.

Figure 2:
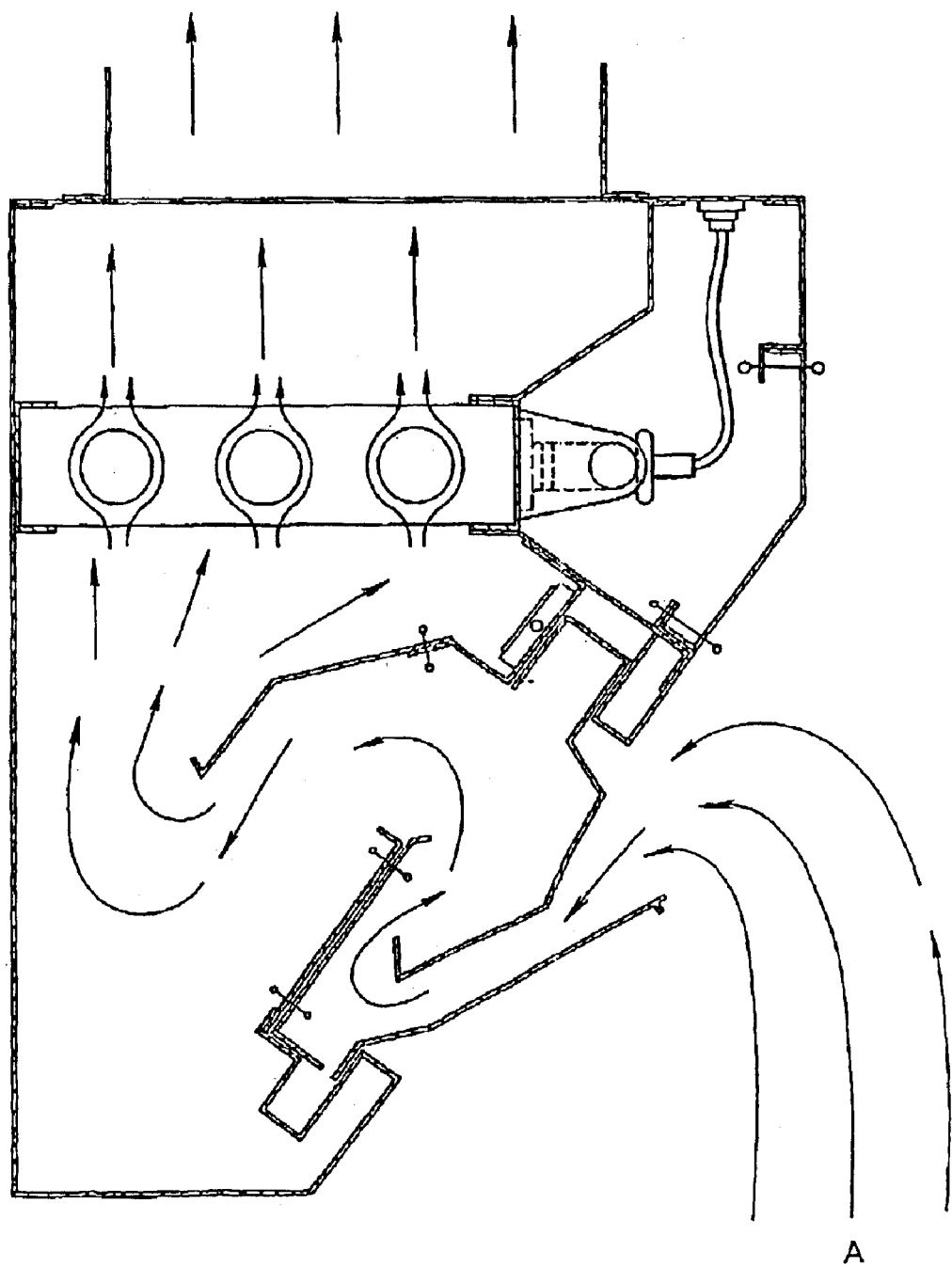
FIG. 2 is the same view of FIG. 1 except for the removal of reference numerals for clarity and the addition of air flow arrows.

It may clearly be seen from FIGS. 1 and 2 that not only is it impossible to trace a direct light path from any of the UV tubes to the region outside the unit, nor can any such path be traced for light reflected from the rear wall 2a, lower wall 2b or indeed any other part of the apparatus.

Figure 3:
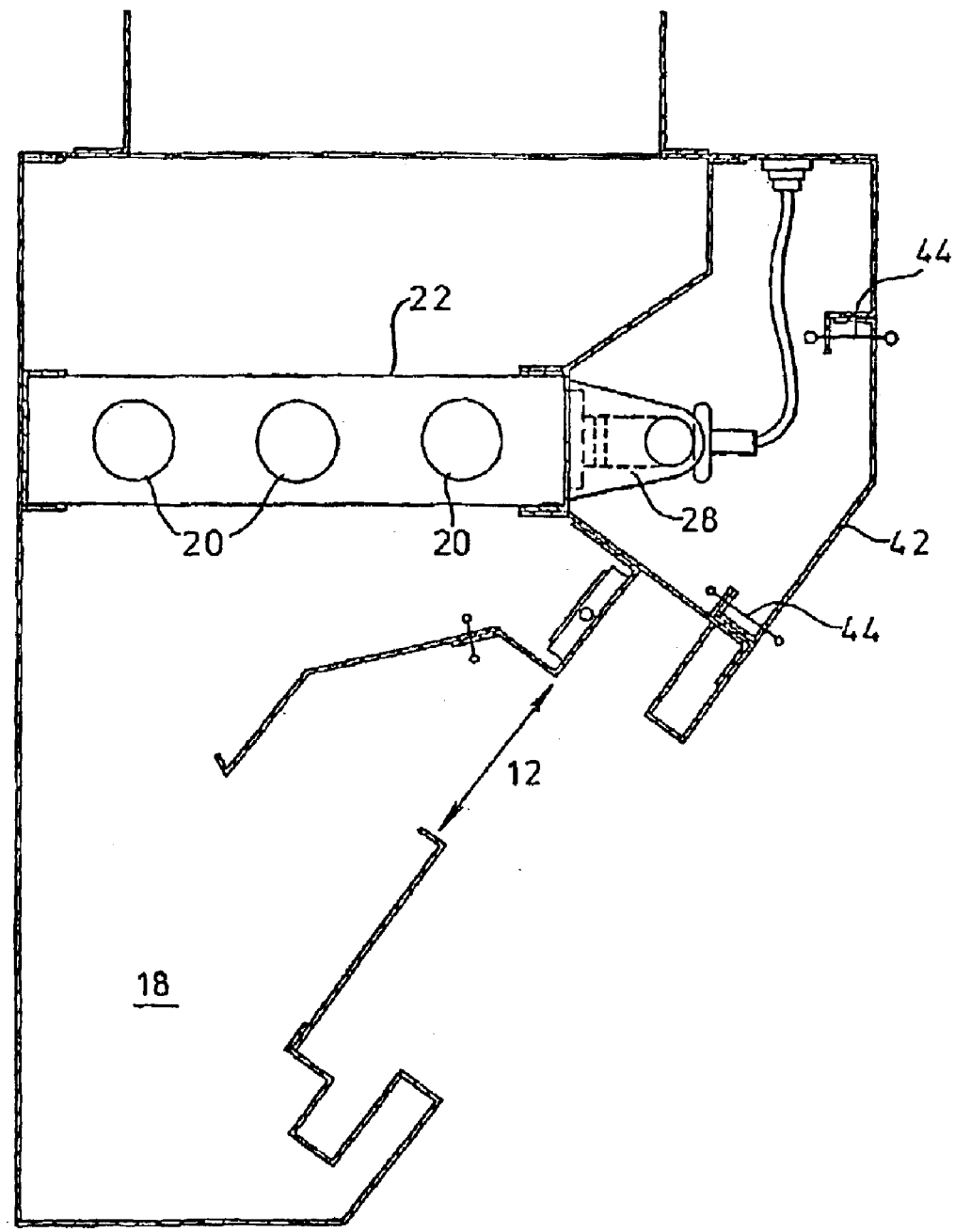
FIG. 3 is a cross-sectional view of the same unit as in FIGS. 1 and 2 with the filter removed.

Turning now to FIG. 3, the same air extraction and treatment unit is shown as in FIGS. 1 and 2, except that this time the grease filter 4 has been removed. If this is done whilst the unit is still operational, the pressure sensor 46 will sense the resultant drop in pressure and cut the supply of electrical power to the UV tubes 20. However, as may clearly be seen, even if the power to the UV tubes 20 were not to be cut for any reason, the internal baffle 14 prevents any direct line of sight between the opening 12 and the UV tubes 20, although it is now possible through a small angle to see the back wall 2a of the plenum 18 and therefore any light reflected from this. However, a warning sticker (not shown) warns the user to switch off the unit if this area should become visible. With the filter 4 removed, the user may gain access to the plenum 18 to clean it periodically. Since the result of the UV oxidation process is fine, dry dust, cleaning is relatively straightforward.

In order to clean or replace any of the UV tubes, an authorised service person possessing the right tool must use it to undo the special screws 44 and remove the front panel 42. The electrical connector 28 may then be removed from the UV cassette 20 and the clips (not shown) retaining the cassette 22 in may be undone. This allows the cassette 22 to be slid out horizontally from the brackets 24, 26 to allow the tubes to be cleaned with a damp cloth and/or replaced.

Figure 4:
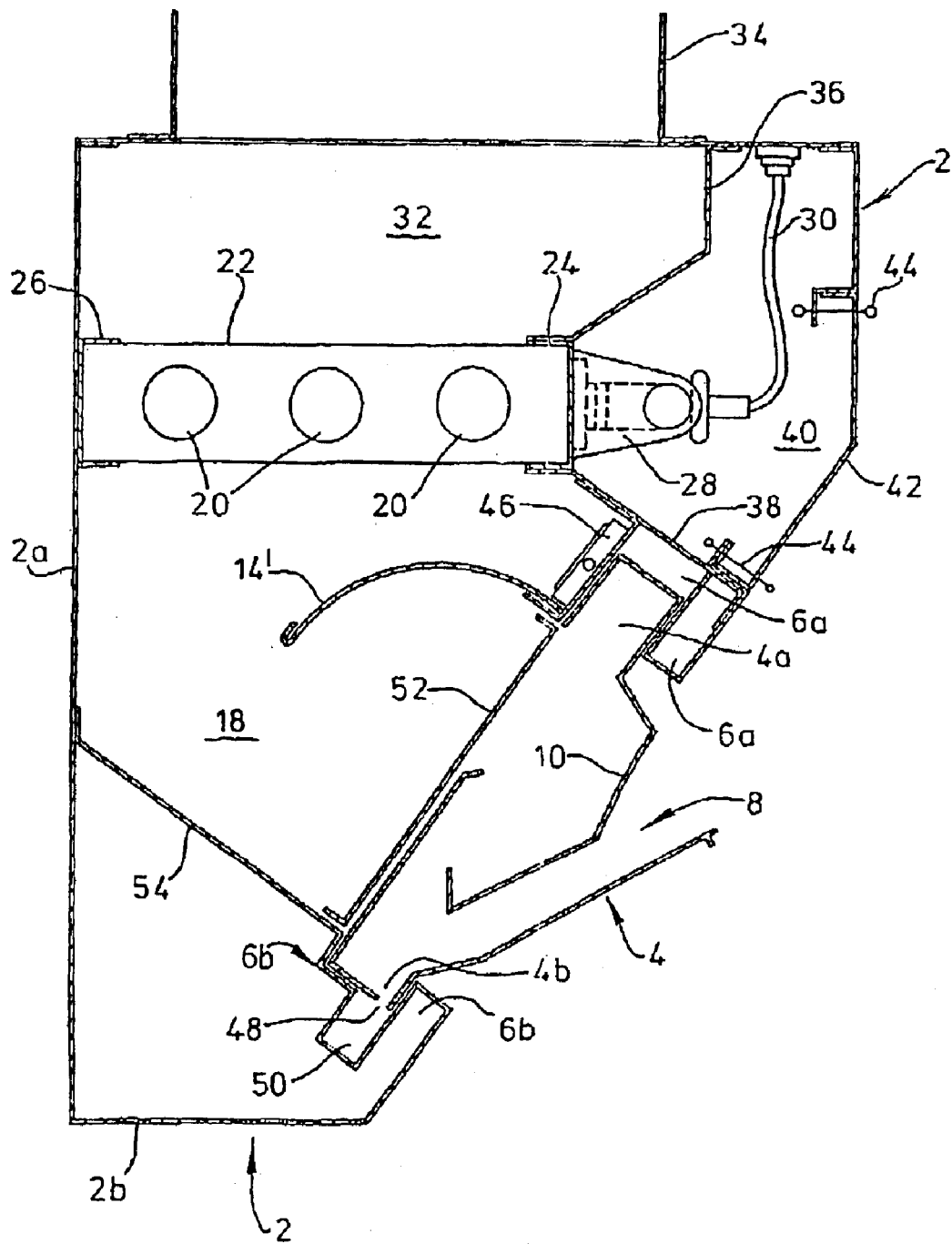
FIG. 4 is a cross-sectional view of a second embodiment of the invention.

A second, preferred embodiment of the invention is shown in the cross-sectional view of FIG. 4. This embodiment is substantially similar to the first and thus only the differences therebetween will be mentioned.

The first difference is that there is no inclined wall extending from the rear of the lower slot 6b to form the opening 12 as there is in FIGS. 1 to 3. Instead, a series of vertical spacers 52 is provided at longitudinally spaced intervals along the apparatus and which extend between the upper and lower slots 6a and 6b. The longitudinal gaps between the spacers 52 are slightly shorter than the width of individual filter units 4 such that the filters 4 overlap the spacers 52 at the edges thereof. The cross-section in FIG. 4 is taken at one such point. This overlapping arrangement further ensures that no direct or reflected UV light from the UV tubes 20 is able to escape from the front of the apparatus.

Secondly a sloping base wall 54 is included, extending from the rear of the plenum 2a to the grease collection channel 50. This wall 54 serves to direct any remaining grease in the chamber 18 into the grease collection channel 50.

Thirdly the upper baffle 14' is curved in profile. Furthermore it is manufactured in longitudinal sections to facilitate removal—e.g. for cleaning etc.

It will be apparent to those skilled in the art that the arrangements described above are just two of many possible examples of how the unit may be arranged in order to prevent direct and reflected light from escaping.

What is claimed is:

1. An air extraction and treatment unit for mounting above a source of contaminated air, said unit comprising an air inlet through which said contaminated air is extracted in use, an air outlet through which decontaminated air is expelled in use, and an air treatment apparatus disposed between said air inlet and said air outlet, said unit defining a path between said air inlet and said air treatment apparatus, said air treatment apparatus having an ultraviolet light source and a barrier in said path between said ultraviolet light source and said air inlet, said barrier for blocking all direct or reflected UV light, wherein the unit is arranged such that in use no direct or reflected ultraviolet light can escape or is visible from outside the unit, the unit further comprising a removable filter disposed in said path at said air inlet, the unit being arranged such that even with the removable filter being removed no direct or reflected UV light from the unit can escape or is visible whereby no UV light will expose and harm a user.

2. A unit as claimed in claim 1, wherein said filter is of the type which forces air flowing therethrough to change direction abruptly.

3. A unit as claimed in claim 1 comprising apparatus for reducing or interrupting the supply of power to the UV source in the event that said filter is removed.

4. A unit as claimed in claim 1 comprising apparatus for reducing or interrupting the power supply to said ultra-violet source in the event that a part of the unit is dismantled.

5. A unit as claimed in claim 3 wherein said apparatus for reducing or interrupting the power comprises pressure sensing apparatus which can sense a drop in pressure inside the unit if the filter or any other part is removed.

6. A unit as claimed in claim 1 comprising a baffle arranged to direct incoming air across the whole area covered by the UV light source or sources.

7. A unit as claimed in claim 4 wherein said apparatus for reducing or interrupting the power comprises pressure sensing apparatus which can sense a drop in pressure inside the unit if the filter or any other part is removed.

8. A ventilation system comprising:

an air inlet having a removable filter disposed thereabout;

an air outlet disposed opposite said air inlet;

an ultraviolet lamp disposed between said air inlet and said air outlet, said ultraviolet lamp for emitting ultraviolet light at a predetermined wavelength, said filter forming a barrier to both direct and reflected light escaping; and a baffle being disposed between said air inlet and said air outlet, said baffle blocking all ultraviolet light emitted from said ultraviolet lamp so that no direct or reflected ultraviolet light can escape or is visible from outside said system, said baffle arranged so that even if said removable filter is removed no direct or reflected ultraviolet light from said system can escape or is visible from outside said system.

* * * * *